United States Patent [19]
Luban et al.

[11] Patent Number: 5,773,225
[45] Date of Patent: Jun. 30, 1998

[54] SCREENING METHOD FOR THE IDENTIFICATION OF COMPOUNDS CAPABLE OF ABROGATION HIV-1 GAG-CYCLOPHILIN COMPLEX FORMATION

[75] Inventors: Jeremy Luban, New York, N.Y.; Stephen P. Goff, Tenafly, N.J.

[73] Assignee: The Trustees of Columbia University in the City of New York, New York, N.Y.

[21] Appl. No.: 248,357

[22] Filed: May 24, 1994

[51] Int. Cl.$^6$ .............................. G01N 33/53; C12Q 1/00; C12N 15/00; C07K 1/00
[52] U.S. Cl. ................................ 435/7.8; 435/4; 435/7.1; 435/172.3; 530/350
[58] Field of Search ............................ 435/5, 7.1, 4, 7.8, 435/172.3; 436/501; 530/350

[56] References Cited

U.S. PATENT DOCUMENTS 5,283,173   2/1994   Fields et al. ................................. 435/6

OTHER PUBLICATIONS

Luban et al., 1993, Human immunodeficiency virus type 1 Gag protein binds to cyclophilins A and B, Cell, 73:1067–1078.

Smith and Johnson, 1988, Single–step purification of polypeptides expressed in *Escherichia coli*, Gene, 67:31–40.

Trono et al., 1989 HIV –1 gag mutants can dominantly interfere with the replication of the wild–type virus, Cell 59:113–120.

DesGroseillers, L., and Jolicoeur, P. (1983) Physical mapping of the Fv–1 tropism host range determinant of BALB/c murine leukemia viruses. J. Virol., 48:685–696.

Fields, S., and Song, O. (1989) A novel genetic system to detect protein–protein reactions. *Nature*, 340:245–246.

Friedmanm, J., and Weissman, I. (1991) Two Cytoplasmic Candidates Candidates for Immunophilin Action are Revealed by Affinity for a New Cyclophilin: One in the Presence and One in the absence of Csa. *Cell*, 66:799–805.

Gill, G., and Ptashne, M. (1987) Mutants of GAL4 Protein Altered in an Activation Function. *Cell*, 51:121–126.

Handschumacher, R. et al., (1984) Cyclophilin: A Specific Cytosolic Binding Protein For Cyclosporin A. Science, 226:544–547.

Hopkins, N., et al., (1977) Six NB–tropic Murine Leukemia Viruses Derived From A B–tropic of BALB/c Have Altered P30. J. Virol., 21:309–318.

Kaelin, W.G., Jr. et al., (1991) Identification of Cellular Proteins That Can Interact Specifically With the T/E1A–Binding Region of the Retinoblastoma Gene Product. *Cell*, 64:521–532.

Liu, J., et al., (1991) Calcineurin Is A Common Target Of Cyclophilin Cyclosporin A and FKBP–FK506 Complexes. *Cell*, 66:807–8015.

Luban, J. and Goff, S. (1991) Binding of Human Immunodeficiency Virus Type 1 (HIV–1) RNA to Recombinant HIV–1 GAG polyprotein. *J. Virol.*, 65:3203–3212.

Luban, J. et al., (1992) Genetic Assay For Multimerization of Retroviral GAG Polyproteins. J. Virol., 66:5157–5160.

McKeon, F. (1991) When Worlds Collide: Immunosuppressants Meet Protein Phosphatases. *Cell*, 66:823–826.

Schreiber, S.L. and Crabtree, G.R. (1992) The Mechanism of Action of Cyclosporin A and FK506. *Immunol. Today*, 13:136–142.

Smith, D.B., and Johnson, K.S. (1988) Single–step Purification of Polypeptides Expressed in *Escherichia coli* as Fusions with Glutathione S–transferase. *Gene*, 67:31–40.

Willis, J.W. and Craven, R.C. (1991) Form, Function and Use of Retro–viral GAG Proteins, *AIDS* 5:639–654.

*Primary Examiner*—Robert D. Budens
*Assistant Examiner*—Jeffrey S. Parkin
*Attorney, Agent, or Firm*—John P. White

[57] ABSTRACT

The human immunodeficiency virus type 1 (HIV-1) gag gene product is capable of directing the assembly of virion particles independent of other viral elements. The Gag protein also plays an important role during the early stages of viral replication. Employing the yeast two-hybrid system, a cDNA expression library was screened and two host proteins identified. These proteins, designated cyclophilins A and B (CyPsA and B), interacted specifically with the HIV-1 Gag polyprotein Pr55$^{gag}$. Glutathione S-transferase-CyP fusion proteins bind tightly to Pr55$^{gag}$ in vitro. Cyclosporin A (CsA) efficiently disrupts the Gag-CyPA binding interaction. The identification of novel compounds capable of abrogating this protein-protein interaction employing the disclosed screening assay will facilitate the development of HIV-1 antiviral agents.

21 Claims, 7 Drawing Sheets

FIGURE 1A

```
CCCCAAAAAAGAGATCCGGATCGGATCCCGGCCGCTCTAGAACTAGTGGATCCCCGGGCTGCAGGAATTC
+-----+-----+-----+-----+-----+-----+
ProProLysLysGluIleProAspArgIleArgGlyArgSerArgThrSerGlySerProGlyLeuGlnGluPhe
GAL4 CODON: 881                                                 SEQUENCE ID NO: 2
GAL4 C-terminus
```

SEQUENCE ID NO: 1

FIGURE 1B

```
GAATTCCTATTAGCCATGGTCAACCCCACCGTG...          SEQUENCE ID NO: 3
+-----+-----+
GluPheLeuLeuAlaMetValAsnProThrVal...           SEQUENCE ID NO: 4

CyP A CODON:    1  2  3  4  5  6
```

FIGURE 1C

```
GAATTCCGGAATTCCATCGGCGGGGTCCGTCTTC...         SEQUENCE ID NO: 5
+-----+-----+
GluPheArgAsnSerIleAlaGlySerValPhe...           SEQUENCE ID NO: 6

CyP B CODON:    10 11 12 13 14 15
```

SCREENING METHOD FOR THE IDENTIFICATION OF COMPOUNDS CAPABLE OF ABROGATION HIV-1 GAG-CYCLOPHILIN COMPLEX FORMATION

The invention disclosed herein was made with Government support under Grant Nos. AI24845 and AI00988 from the National Institute of Allergy and Infectious Disease. Accordingly, the U.S. Government has certain rights in this invention.

Throughout this application, various references are referred to by author and year within parentheses. Disclosures of these publications in their entireties are hereby incorporated by reference into this application to more fully describe the state of the art to which this invention pertains. Full bibliographic citation for these references may be found at the end of this application, preceding the claims.

BACKGROUND OF THE INVENTION

The gag gene of human immunodeficiency virus type 1 (HIV-1) and related retroviruses is expressed as a precursor polyprotein that possesses the information necessary for virion particle formation and release from the host cell membrane (for review see Wills and Craven, 1991). At the time of virion release, the polyprotein is cleaved by the pol-encoded protease to produce several proteins, including the matrix protein, which lines the virion membrane envelope; the capsid protein (CA), which forms the core of the virion; and the nucleocapsid protein, which coats the genomic RNA. Little is known about host protein necessary for Gag protein folding or transport, although targeting of the Gag polyprotein to the cell membrane requires cotranslational modification by the host N-myristoyl transferase (Gottlinger et al., 1989; Rein et al., 1986 and Rhee and Hunter, 1987).

Upon entry into a new host cell, the viral RNA genome is reverse transcribed by the pol-encoded reverse transcriptase, and the resulting double-stranded DNA is integrated into the host genome to form the provirus (for a review see Weiss et al., 1984). During these early steps of infection, the unintegrated viral genome is contained within a nucleoprotein complex that probably contains Gag protein. Direct analysis of unintegrated DNA from acutely infected cells has demonstrated that it is associated with CA (Bowerman et al., 1989). Engineered point mutations in CA have been identified that assemble noninfectious virion particles; these virions appear to be blocked early in the infectious cycle (Hsu et al., 1985; Strambio-deCastillia and Hunter, 1992). A dominant genetic restriction limits the efficiency of integration of certain murine retroviral strains (Lilly and Pincus, 1973). This viral tropism maps to CA (DesGroseillers and Jolicoeur, 1983; Hopkins et al., 1977). Thus, Gag protein not only plays an important role in virion assembly, but also in early events after infection, and at any of these stages, Gag-host protein interactions may play an important role.

The yeast two hybrid system is a method for studying protein-protein interactions (Fields and Song, 1989; Fields et al., U.S. Pat. No. 5,283,173). Yeast with an integrated copy of a GAL1-lacZ indicator gene are cotransformed with two plasmids, each encoding a different GAL4 fusion protein. One plasmid encodes a fusion between the GAL4 DNA-binding domain and protein X, and the second plasmid encodes a fusion between the GAL-4 activation domain and protein Y. If proteins X and Y interact, then the two domains of GAL4 are brought to the same physical location, activating transcription from the lacZ gene. It has been previously shown that the yeast GAL4 two hybrid system could be used to study the multimerization of retroviral Gag polyproteins (Luban et al., 1992). When X and Y are Gag polyproteins from the same retrovirus, β-galactosidase (β-gal) activity is produced. If X and Y are different Gag polyproteins from genetically divergent retroviruses, no β-gal activity is detected. The yeast two hybrid system has been used successfully to screen cDNA expression libraries for genes encoding proteins that interact with a given protein of interest (Chevray and Nathans, 1992; Chien et al., 1991; Hardy et al., 1992; Yang et al., 1992 and Zervos et al., 1993). Yeast are cotransformed with a plasmid expressing the GAL4 DNA-binding domain fused to the protein of interest and a pool of plasmids encoding GAL4 activation domain-cDNA library fusion proteins.

A human library was screened for encoded proteins capable of binding to the HIV-1 Gag polyprotein Pr55$^{gag}$. Two proteins were identified, cyclophilins (CyPs) A and B. The CyPs were originally identified as cellular proteins that bind the immunosuppressive drug cyclosporin A (CsA) (Hanschumacher et al., 1984), and a great deal is known about how CsA inhibits T cell activation pathways (McKeon, 1991; Schreiber and Crabtree, 1992). The Pr55$^{gag}$ binding to the cellular target of the immunosuppressive drug CsA is extremely intriguing, since the most obvious laboratory abnormality in people infected with HIV-1 is the inevitable progression toward a profound depletion of CD4$^+$ T cells (Pantaleo et al., 1993). In addition, there are functional T cell defects prior to the quantitative depletion of CD4 cells (Fauci, 1988). A Gag-CyP interaction may play an important role in acquired immunodeficiency syndrome (AIDS) immunopathology.

SUMMARY OF THE INVENTION

This invention is directed to methods for determining whether a compound is capable of interfering with the formation of a complex between a retrovirus Gag protein and a cyclophilin. The invention further provides for a method of disrupting a retrovirus life cycle in a mammal which comprises administering to the mammal a compound which is capable of disrupting a retrovirus Gag protein-cyclophilin interaction so as to thereby disrupt the retrovirus life cycle. The compound administered to the mammal may be a chemical molecule, cyclosporin A, Gag protein or fragments thereof.

BRIEF DESCRIPTION OF THE FIGURES

FIG. 1A SEQ ID NOS. 1–2. Sequences at the joints of GAL4-cDNA Fusion Constructs. The sequence from pGADNOT at the joint between the GAL4 activation domain coding sequences and the EcoRI site used in the original construction of the HL-60 CDNA library is shown. The sequence encoding the five carboxy-terminal amino acids of GAL4 (codons 877–881) is underlined (SEQ ID NOS.: 1–2).

FIG. 1B (SEQ ID NOS. 3–4 and FIG. 1C (SEQ ID NOS. 5–6 The sequences at the 5' end of the cDNA inserts in clones 2.1 (B) (SEQ ID NOS. 3–4 and 4.1 (C) (SEQ ID NOS. 5–6 are shown. CyP sequences are underlined, and the first six CyP codons of each are noted. EcoRI sites used for cloning are shown in bold letters.

FIG. 7A Bacterial lysate containing GST-CyPA was incubated with buffer alone (lane 1). 80 mM CsA (lane 2), bacterial lysate containing Pr55$^{gag}$ (lane 3), or control bacterial lysate (lane 4) for 1 hour at 4° C. Two micrograms of CN (0.1 μM) and 2 μg of calmodulin (0.5 μM) were added to each reaction and incubated for an additional 1 hour. G beads were added and washed three times, and bound protein was subjected to SDS-PAGE and Western blotting with anti-CN β subunit antibody. A sample of CN was applied directly (lane 5). The arrow indicates the position of migration of the CN β subunit. FIG. 7B GST-CyPB (lanes 2, 3 and 5–7), GST (lane 4), Pr55$^{gag}$ (lane 8), or GPr55$^{gag}$ (lane 9) was incubated with G beads using the standard conditions. G beads with bound protein were washed twice and incubated with 80 mM CsA (lane 2), 8 mM CsA (lane 3), control bacterial lysate (lane 6) or bacterial lysate containing Pr55$^{gag}$ (lane 7), or buffer alone (lanes 4, 5, 8 and 9). G beads and bound protein were washed twice and incubated in buffer with CN (0.1 μM) and calmodulin (0.5 μM). G beads were washed three times, and bound protein was subjected to SDS-PAGE and Western blotting with anti-CN β subunit antibody. A sample of the input CN without beads was applied directly (lane 1).

DETAILED DESCRIPTION OF THE INVENTION

Figure 2:
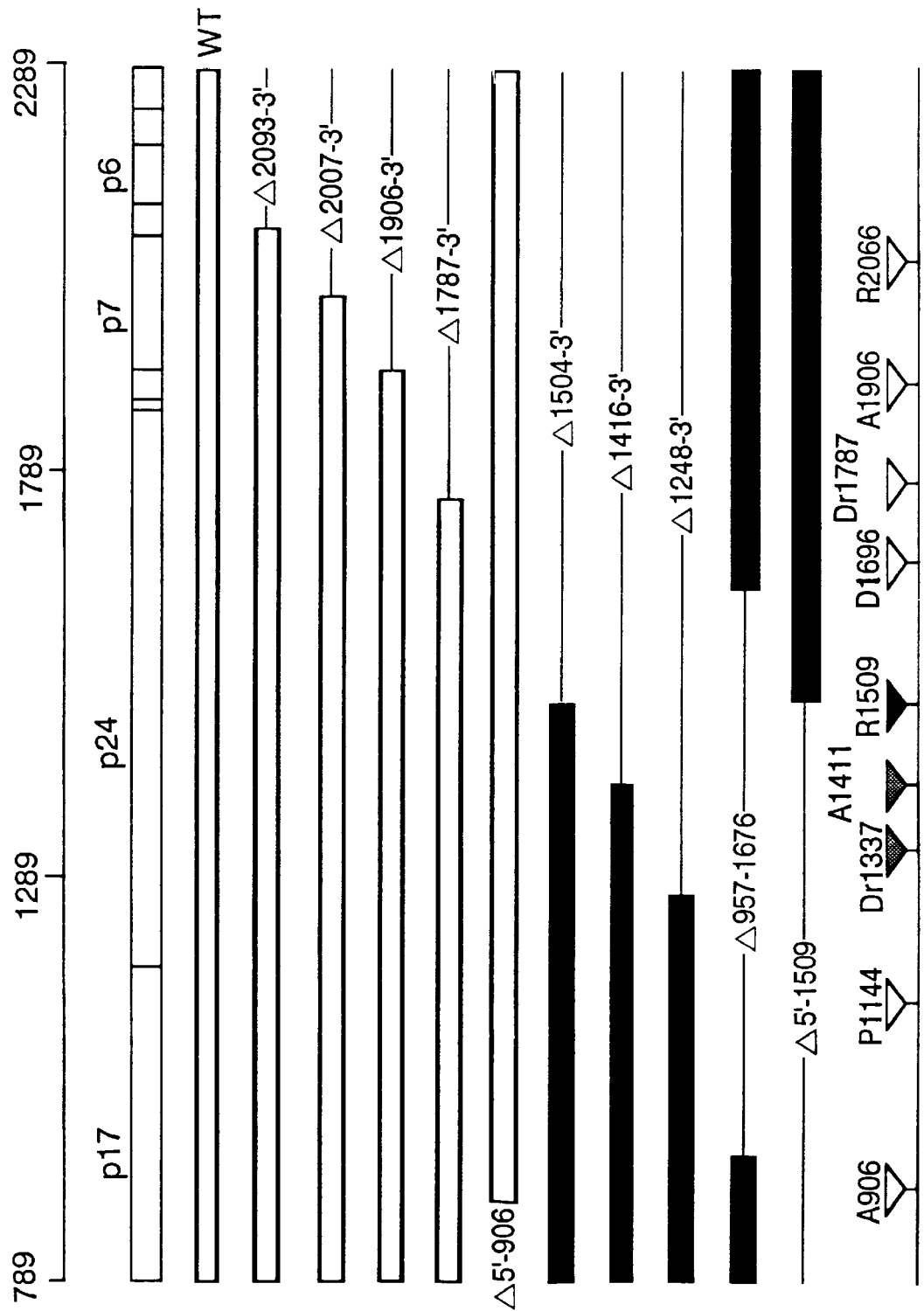
FIG. 2. The Effect of Mutations in Pr55$^{gag}$ on the Ability of Gag-GAL4 Fusion Proteins to Activate β-Gal Activity in Yeast Cotransformed with GAL4-CyP Fusion Protein Expression Plasmids. Mutant forms of Pr55$^{gag}$ were subcloned into pGAL4DB-HG. A schematic of the gag coding sequence is shown, and sequence numbers indicated the nucleotide position in the HXB2C provirus with respect to the 5' end of the 5' long terminal repeat. The names of the mutants indicate the nucleotide sequences deleted or the location of linker inserts. Coding sequences retained by the mutants are shown with a box. Linker insertion mutations are denoted with a triangle. Yeast strain GGY1::171, which carries a GAL1-lacZ fusion gene integrated into the chromosome, was cotransformed with each mutant plasmid against plasmid 2.1 and against plasmid 4.1. Colonies were replica-plated onto nitrocellulose filters and scored for β-gal activity by incubation with X-Gal. Open boxes or triangles indicate that when tested against either 2.1 or 4.1, the mutant had activity equivalent to that of the wild-type (WT) Pr55$^{gag}$. Closed boxes indicate that the mutant had no detectable activity against 2.1 or against 4.1. Stippled triangles indicate no activity against 2.1; against 4.1, Dr1337 had weakly detectable activity and A1411 reacted like wild type.

This invention is directed to a method for determining whether a compound is capable of interfering with the formation of a complex between a retrovirus Gag protein and a cyclophilin, which comprise the following steps:

a) incubating the compound with an appropriate cylophilin affinity fusion protein and the Gag protein;

b) contacting the incubate of step (a) with an appropriate affinity medium under conditions so as to bind the cyclophilin affinity protein complex, if such a complex forms; and c) measuring the amount of the cyclophilin affinity protein complex formed in step (b) so as to determine whether the compound is capable of interfering with the formation of the complex between the retrovirus Gag protein and the cyclophilin.

In one preferred embodiment the cyclophilin is selected from the group comprising cyclophilin A, B, C or D or combinations thereof. The affinity fusion protein may be GST-CyP and the Gag protein may be Pr55$^{gag}$ or p24. The affinity medium may be glutathione-agarose beads. The bound affinity protein may be analyzed using monoclonal or polyclonal antibodies. The above method may also be performed using an appropriate retrovirus Gag affinity fusion protein. In one embodiment the Gag protein or cylophilin protein may be labelled with a detectable moiety selected from a group consisting of a fluorescent label, a radioactive atom, and a chemiluminescent label. The cyclophilin affinity protein complex or the retrovirus Gag affinity protein complex may be bound to the affinity medium. The cyclophilin affinity protein complex or the retrovirus Gag affinity protein complex may be purified and removed from the affinity medium and the amount of the Gag protein or cyclophilin may be determined. The above assays may be performed in vivo or in vitro.

The above assay can also be extended to assays using protein expressed in baculovirus, tissue culture cells or Gag purified from virus. A further embodiment of the invention is the use of an ELISA assay, in which cyclophilin protein is bound to the bottom of 96-well plates; Gag protein is added, and binding is detected using anti-Gag antibodies. In addition Gag protein may be labelled with a radioisotope, or a chemical marker such as biotin or β-galactosidase, thus precluding the need for an antibody for detection of binding.

The invention also provides a method of disrupting a retrovirus life cycle in a cell which comprises contacting the cell with a compound which is capable of disrupting a retrovirus Gag protein-cyclophilin interaction so as to thereby disrupt the retrovirus life cycle. The compound contacting the cell may be chemical molecule, cyclosporin, Gag protein or fragments thereof. Other compounds contacting the cell may be cylophilin or fragments thereof.

The invention further provides for a method of disrupting a retrovirus life cycle in a mammal which comprises administering to the mammal a compound which is capable of disrupting a retrovirus Gag protein-cyclophilin interaction so as to thereby disrupt the retrovirus life cycle. The compound administered to the mammal may be, a chemical molecule, cyclosporin A, Gag protein or fragments thereof. Other compounds administered to the mammal may be cylophilin or fragments thereof.

For the above-identified compounds and methods the retrovirus may be selected from the following groups, Avian leukosisarcoma, Mammalian C-type, B-type viruses, D-type viruses, HTLV-BLV group, Lentiviruses and "Foamy viruses. The retroviruses may also be selected from the following examples, Rous sarcoma virus (RSV), Avian myeloblastosis virus (AMV), Avian erythroblastosis virus (AEV), Rous-associated virus (RAV)-1 to 50, RAV-0, Moloney murine leukemia virus (Mo-MLV), Harvey murine sarcoma virus (HA-MSV), Abelson murine leukemia virus (A-MuLV), AKR-MuLV, Feline leukemia virus (FeLV), Simian sarcoma virus, endogenous and exogenous viruses in mammals, Reticuloendotheliosis virus (REV), spleen necrosis virus (SNV), Mouse mammary tumor virus (MMTV), Mason-Pfizer monkey virus (MPMV), "SAIDS" viruses, Human T-cell leukemia (or lymphotropic) virus (HTLV), Bovine leukemia virus (BLV), Human immunodeficiency virus (HIV-1 and -2), Simian immunodeficiency virus (SIV), Feline immunodeficiency virus (FIV), SSV, REM, Visna/Maedi virus, Equine infectious anemia virus (EIAV), Caprine arthritis-encephalitis virus (CAEV), Progressive pneumonia virus, many human and primate isolates e.g., simian foamy virus (SFV).

This invention is also directed to pharmaceutical compositions comprising therapeutically effective amounts of compounds of the invention together with suitable diluents, preservatives, solubilizers, emulsifiers and adjuvants. Administering a therapeutically effective amount refers to that amount which provides therapeutic effect for a given condition and administration regime. Such compositions are liquids or lyophilized or otherwise dried formulations and include diluents of various buffer content (e.g., Tris-HCL, acetate, phosphate), pH and ionic strength, additives such as albumin or gelatin to prevent adsorption to surfaces, detergents (e.g., Tween 20, Tween 80, Pluronic F68, bile acid salts), solubilizing agents (e.g., glycerol, polyethylene glycol), anti-oxidants (e.g., ascorbic acid, sodium metabisulfite), preservatives (e.g., Thimerosal, benzyl alcohol, parabens), bulking substances or tonicity modifiers (e.g., lactose, mannitol), complexation with metal ions, or incorporation of the material into or onto particulate preparations of polymeric compounds such as polylactic acid, polyglycolic acid, hydrogels, etc. or into liposomes, microemulsions, micelles, unilamellar or multilamellar vesicles, erythrocyte ghosts, or spheroplasts. Such compositions will influence the physical state, solubility, stability, rate of in vivo release. Controlled or sustained release compositions include formulation in lipophilic deposits (e.g., fatty acids, waxes, oils). Also included in this invention are particulate compositions coated with polymers (e.g., poloxamers or poloxamines). Other embodiments of the compositions of the invention incorporate particulate forms protective coatings and permeation enhancers for various routes of administration, including parenteral, pulmonary, nasal and oral.

The following examples are offered to more fully illustrate the invention, but are not to be construed to limit the scope thereof.

Identification of cDNAs Encoding Proteins that Interact with Pr55$^{gag}$ Using the Two Hybrid System To identify host proteins that interact specifically with Pr55$^{gag}$, a library of plasmids that express GAL4 activation domain-cDNA expression library fusion proteins was first created. Inserts from an undifferent human leukemia cell line (HL-60) cDNA library were subcloned into a GAL4 activation domain expression plasmid, PGADNOT, and five pools were collected, each consisting of more than 150,000 bacterial colonies.

Saccharomyces cerevisiae strain GGY1::171 containing a GAL4-responsive lacZ gene (Gill and Ptashne, 1987) was transformed with pGAL4DB-HG (Luban et al., 1992), encoding a GAL4 DNA-binding domain-Pr55$^{gag}$ fusion protein, and transformants were selected for histidine prototrophy. These lines were then transformed with the pGADNOT-cDNA library DNA, selecting for leucine prototrophy. Cotransformants were plated at a density of approximately 3000 colonies per 100 mm plate. Nitrocellulose replicas of the colonies were assayed for β-gal activity by freeze fracturing the cells and incubating in buffer containing 5-bromo-4-chloro-3-indolyl-β-D-galactoside (X-Gal)(Breedon and Nasmyth, 1985). Colonies were considered to express β-gal activity if they turned blue within 8 hours.

Of 500,000 colonies screened for β-gal activity, 20 were scored as positive. Eleven pGADNOT cDNA plasmids were successfully isolated, and all produced β-gal activity when retested against pGAL4DB-HG in GGY1::171 (Table 1). (1.3) gave a highly significant match with sequences from GenBank (Table 1). Of the nine false positive clones, eight

TABLE 1

HL-60 cDNA Library pGADNOT Clones Promoting β-GAL Activity in Yeast Cotransformed with pGAL4DB-HG

| Clone[b] | Insert size (Number of Nucleotides) | GeneBank Match (Locus; Accession #) | β-GAL Activity in Yeast[a] | | |
|---|---|---|---|---|---|
| | | | Versus pGAL4DB-HG | Versus pGAL4DB | Clone Alone |
| 2.1 | 1,300 | Human mRNA for T cell CyPA (GB:HUMCYCR; Y00052) | + | — | — |
| 4.1 | 900 | Human CyPB mRNA (GB: HUMCYPBA; M60857) | + | — | — |
| 3.1 | 620 | Rat mRNA for ribosomal protein L8 (GB:RATRPL8; X62145) | + | + | — |
| 3.2 | 560 | Rat mRNA for ribosomal protein L23a (GB: RATRPL23A; X65228) | + | + | — |
| 2.2 | 650 | Chicken mRNA for ribosomal protein L27 (GB:CHKRPL27; X56852) | + | + | — |
| 1.4, 1.5, 2.4 | 400 | Yeast YL41A gene for ribosomal protein YL41 (GB: YSCYL41A; X16065) | + | + | — |
| 3.3 | 250 | Human 28S ribosomal RNA gene (GB:HUMRGM; M11167) | + | + | — |
| 2.3 | 650 | Human autoantigen small nuclear ribonucleoprotein Sm-D mRNA (GB:HUMSNRNPD; J03798) | + | + | — |
| 1.3 | 1,300 | No match | + | + | — |

[a]The first number refers to the library pool, the second to the individual clone.
[b]Following plasmid isolated in bacteria, pGADNOT-cDNA clones were retransformed into yeast strain GGY1::171 using standard methods (Becker and Guarente, 1991) with the indicated plasmids. Colonies were lifted and stained for β-gal activity as described (Breedon and Nasmyth, 1985). Entries indicate the presence or absence of blue color with transformants.

Two of the clones (2.1 and 4.1) were more active than the others; while some of the clones required as much as 8 hours before activity was detectable, these two clones were clearly positive within 10 minutes. Though none of the plasmids produced β-gal activity when singly transformed into yeast, nine of the clones were active when cotransformed with pMA424, the parent plasmid encoding the GAL4 DNA-binding domain without Pr55$^{gag}$. This result suggested that these nine clones did not depend on the presence of the Pr55$^{gag}$ protein for activity. The two true positive clones (2.1 and 4.1) were the clones that produced the most activity in combination with pGAL4DB-HG.

To test whether the activity of these clones was somehow peculiar to transcriptional regulation by GAL4, all 11 pGADNOT clones were tested for the ability to produce β-gal activity in a different yeast strain, CTY 10–5d, which possesses an operator with lexA-binding sites upstream of the transcriptional start site of the GAL1-lacZ gene. Each of the 11 PGADNOT clones produced β-gal activity when cotransformed with a plasmid encoding a lexA-Pr55$^{gag}$ fusion protein. Curiously, unlike the false positive activity detected with 9 of the 11 clones using the GAL-4 system, none of the clones produced β-gal activity when co-transformed with the parent lexA plasmid that contained no Pr55$^{gag}$ sequences. Thus, all 11 clones seemed to exhibit Pr55$^{gag}$-dependent activation in this system.

cDNA Clones Identified in the Genetic Screen Encode RNA-Binding Protein and CyPs DNA sequences were obtained for the inserts of the 11 clones identified in the genetic screen, and all but one clone were found to encode proteins with RNA binding activity. This finding suggests that some property of these clones (either the RNA binding activity itself or, perhaps, merely the presence of basic amino acids) contributes to the false positivity.

The two true positive clones, 2.1 and 4.1, encoded two proteins of the same family, CyPA and CyPB. The sequences at the 5' end of the inserts of clones 2.1 and 4.1 are shown in FIG. 1B and 1C, respectively. The insert in clone 2.1 begins in the 5' untranslated portion of the CyPA RNA, 9 nt before the initiator methionine, and continues through the entire open reading frame past the non-coding sequences at the 3' end of the gene. The insert in clone 4.1 begins at the tenth codon of CyPB and continues through the open reading frame past the 3' noncoding sequences of the gene. In subsequent screening of the same pools, recovered three additional plasmids containing CyPB cNDAs were recovered; one of these was identical to clone 4.1, and two have distinct junction positions at the 5' end.

Fragments of Pr55$^{gag}$ Fused to the GAL4 DNA-Binding Domain Retain the Ability to Activate Transcription in Yeast Expressing GAL4-CyP Fusion Proteins To localize the portion of Gag that mediates binding to the CyPs, the effect on binding of mutations in the Pr55$^{gag}$ coding sequence was examined. A panel of mutants, including deletions of 5' and internal coding sequences and insertions of linkers with stop codons (FIG. 2), was transferred into the expression vector encoding the GAL4 DNA-binding domain. Each of these plasmids encodes a stable fusion protein of the expected size detected on Western blot (Luban et al., 1993). None of these fusion proteins was capable of activating lacZ activity independently. These plasmids were tested for the ability to activate transcription from the lacZ gene in yeast cotransformed with either of the two GAL4 activation domain-CyP fusion protein expression plasmids (FIG. 2). In all cases, the results were the same for the CyPA and the CyPB fusion proteins, gag sequences 5' of nucleotide 906 and 3' of nucleotide 1787 could be deleted with no effect on activity; these regions clearly were not essential for the interaction of Pr55$^{gag}$ with CyP proteins.

Nine linker insertion mutations in the Pr55$^{gag}$ coding sequence, each with a 12 nt insertion, were tested for their effects on binding to the CyPs. of the nine linker mutations, three had effects on Pr55$^{gag}$-Cyp interactions (FIG. 2). Mutant R1509 disrupted binding to either CyPA or CyPB. Mutants Dr1337 and A1411 were unable to binding to CyPA; Dr1337 was partially disruptive of binding to CyPB, but A1411 had no effect on binding to CyPB. The three disruptive mutants cluster within the 5' half of the CA coding sequences. Taken together, the results of the analysis with the Pr55$^{gag}$ deletion and linker insertion mutants demonstrate that the part of Pr55$^{gag}$ necessary for binding to the CyPs lies within the amino-terminal two-thirds of CA and the carboxy-terminal half of the matrix protein.

CyPs Do Not Bind Gag Polyproteins of Retroviruses Distantly Related to HIV-1

The Gag polyproteins of simian immunodeficiency virus type 1 (SIV-1), Mason-Pfizer monkey virus (MPMV), and Moloney murine leukemia virus (MoMLV), as well as the integrase protein (IN) of HIV-1 were tested to determine whether they were capable of interacting with the CyP proteins in the two hybrid system. Each retroviral Gag polyprotein, as well as IN, is capable of forming homomultimers (J.L and S.P.G., unpublished data; G.V.K. and S.P.G., submitted). As shown previously, HIV-1 Pr55$^{gag}$ showed activity against both CyPA and CyPB (Table 2).

TABLE 2

β-Gal Activity in Yeast Expressing GAL4 Hybrid Proteins[a]

| Plasmid | Gene fused to GAL4 DNA-binding Domain | β-GAL Activity | | |
|---|---|---|---|---|
| | | Versus Clone 2.1 | Versus Clone 4.1 | Clone Alone |
| pGAL4DB-HG | HIV-1 Pr55$^{gag}$ | + | + | — |
| pGAL4DB-SG | SIV$_{mac230}$ Pr57$^{gag}$ | — | + | — |
| pGAL4DB-MPG | MPMV pr76$^{gag}$ | — | — | — |
| pGAL4DB-MG | MoMLV Pr65$^{gag}$ | — | — | — |
| pGAL4DB-IN | HIV-1 p32 (IN) | — | — | — |

[a]Yeast strain GGY1::171 was transformed with the indicated plasmids using standard procedures (Becker and Guarente, 1991). Yeast colonies were lifted and stained for β-gal activity as described (Breedon and Nasmyth, 1985). Entries indicate the presence or absence of blue color with transformants.

The Gag polyprotein of SIV also had activity against CYPB but not against CyPA. The Gag polyproteins of MPMV or MOMLV and of HIV-1 IN had no detectable activity against either of the CyPs tested. The Gag polyproteins of HIV-1 and closely related retroviruses interact with the CyP proteins, but that the Gag polyproteins of more distantly related retroviruses are not capable of carrying out this interaction.

CyPs Bind Pr55$^{gag}$ In Vitro

Figure 3:
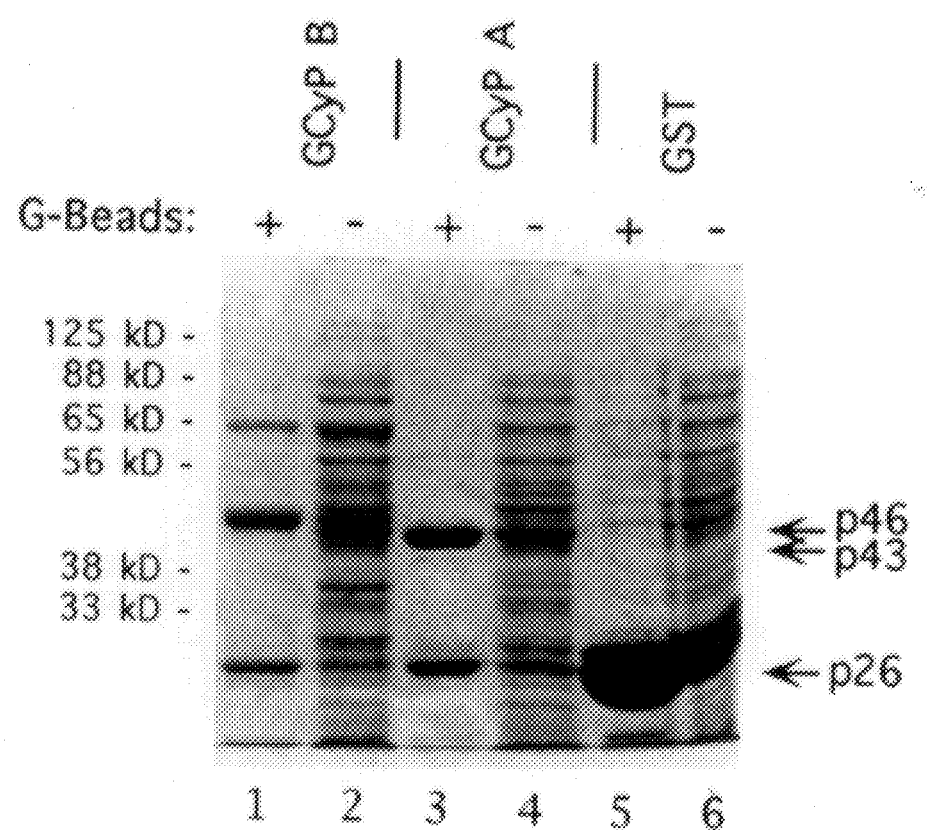
FIG. 3. Expression and Affinity Purification of GST-CyP Fusion Proteins. Protein expression was induced in bacteria transformed with GST expression plasmids according to standard methods. Total bacterial lysates (lanes 2, 4, and 6) and lysates purified on G beads (lanes 1, 3 and 5) were subjected to SDS-PAGE, and the gel was stained with Coomassie blue. Bacteria were transformed with pGCyPB (lanes 1 and 2), pGCyPA (lanes 3 and 4), and pGEX-2T (lanes 5 and 6). The positions of size markers, GST (p26), GST-CyPA (p43), and GST-CyPB (p46) are indicated.

To demonstrate in vitro binding of Gag polyproteins to the CyPs, inserts from clones 2.1 and 4.1 were first subcloned into a bacterial expression plasmid, to express the CyP proteins as glutathione S-transferase (GST) fusion proteins. GST fusion proteins may be purified in a single step using glutathione-agarose beads (G beads) (Smith and Johnson, 1988), and this system has been used to demonstrate protein-protein interactions in vitro (Kaelin et al., 1991). In addition, other groups have shown that GST-CyP fusion proteins retain both peptidylprolyl cis-trans isomerase and drug binding activities (Friedman and Weissman, 1991; Liu et al., 1991). The resulting plasmids, pGCyPA and pGCyPB, encoding GST-CyPA and GST-CyPB fusion proteins, were transformed into bacteria. Following induction with isopropyl-β-D-thiogalactopyranoside, the fusion proteins GST-CyPA (FIG. 3, lane 4) and GST-CyPB (FIG. 3, lane 2) constituted a significant fraction of the total bacterial protein in crude lysates. The fusion proteins were readily recovered by incubating the soluble fraction of the total bacterial lysate with G beads and washing the beads three times. The purity of the proteins could be assessed by electrophoresis after elution with sodium dodecyl sulfate (SDS) (FIG. 3). Roughly 70% of the protein had the expected mobility for the CyP fusion proteins. Additional proteins corresponding to the mobility of GST alone, as well as several unidentified bands of slower mobility, were detected.

Figure 4A:
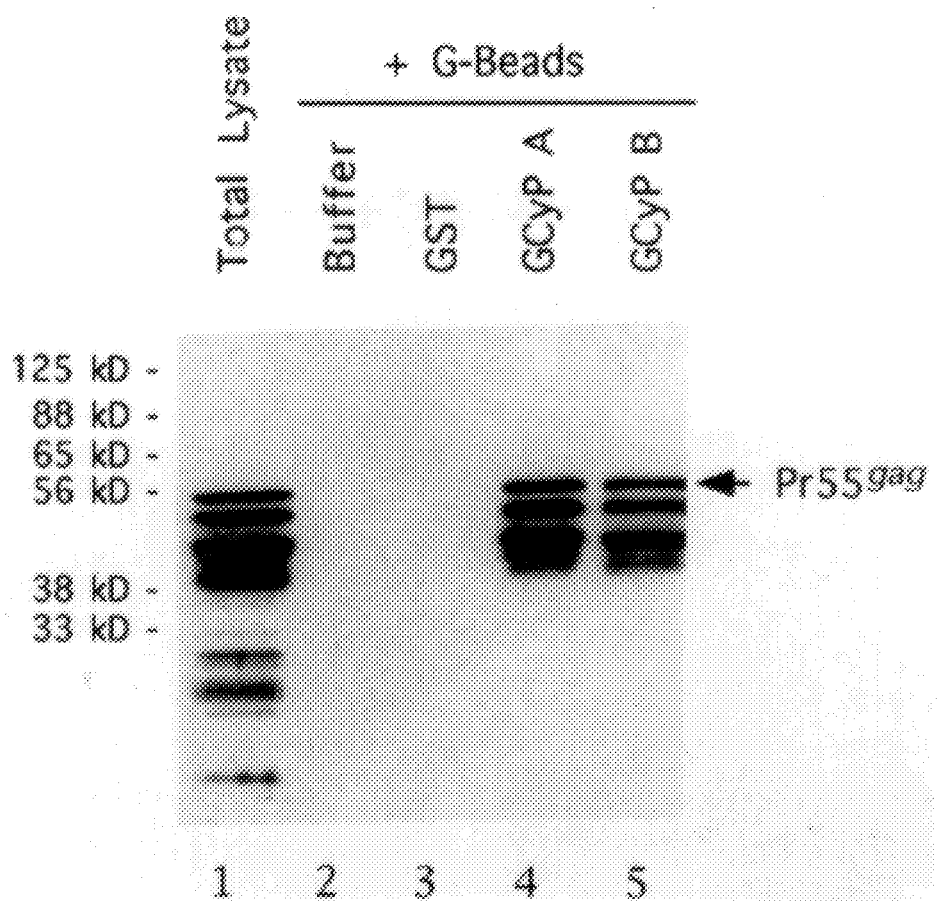
FIG. 4A. Western Blot Demonstrating Specific Binding of Pr55$^{gag}$ to GST-CyP Fusion Proteins. Total lysate from bacteria expressing pr55$^{gag}$ was incubated with buffer alone (lane 2) or with lysates from bacteria expressing GST (lane 3), GST-CyPA (lane 4), or GST-CyPB (lane 5). GST proteins were collected with G beads and analyzed by SDS-PAGE. Protein was electroblotted to a nitrocellulose membrane and probed with mouse anti-p24 monoclonal antibody and peroxidase-linked sheep anti-mouse immunoglobulin. Total lysate from bacteria expressing Pr55$^{gag}$ is shown in lane 1. The position of Pr55$^{gag}$ is shown; additional bands seen are carboxy-terminal degradation products of Pr55$^{gag}$ (Luban and Goff, 1991).

As a source of Pr55$^{gag}$ protein, a preparation of total soluble protein from bacteria transformed with pT7HG (pro⁻) (Luban and Goff, 1991) was first used. In addition to intact Pr55$^{gag}$, two smaller degradation products are reproducibly seen on Western blot with anti-p24 monoclonal antibody (FIG. 4A, lane 1). When the Gag protein was incubated with lysates containing either GST-CyPA or GST-CyPB prior to or concurrent with the addition of G beads, Pr55$^{gag}$ was quantitatively recovered and easily detected on Western blot (FIG. 4A, lanes 4 and 5) or on Coomassie blue-stained gels. In control experiments, no detectable Gag protein bound to G beads alone (FIG. 4A, lane 2) or to GST bound to G beads (FIG. 4A, lane 3).

Figure 4B:
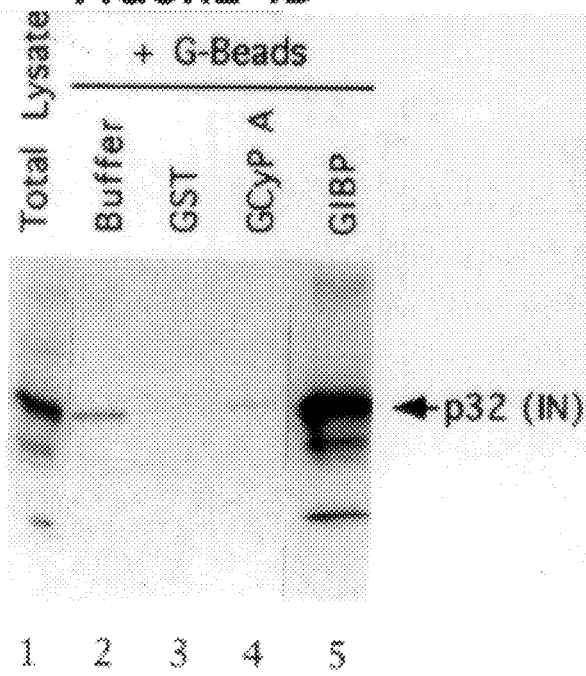
FIG. 4B. Western Blot Demonstrating Specific Binding of p32 to GST-CyP Fusion Proteins. Total lysate from bacteria expressing HIV-1 IN (p32) was incubated with buffer alone (lane 2) or with lysates from bacteria expressing GST (lane 3), GST-CyPA (lane 4), or GIBP (lane 5). G beads were added, and samples were processed as in (A), except that the blot was probed with mouse anti-IN monoclonal antibody and peroxidase-linked sheep anti-mouse immunoglobulin. Input bacterial lysate expressing IN is shown in lane 1.
Figure 4C:
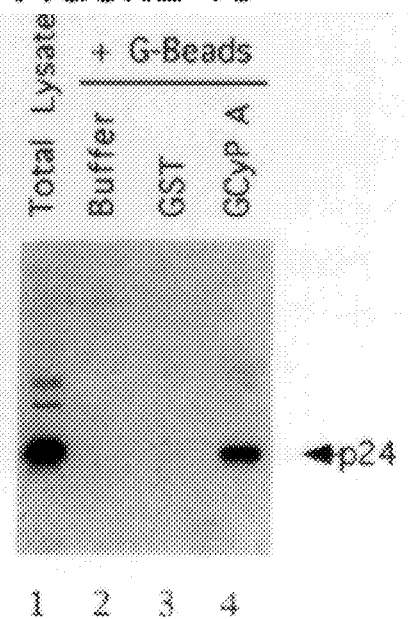
FIG. 4C. Western Blot Demonstrating Specific Binding of p24 to GST-CyP Fusion Proteins. Total lysate from bacteria expressing p24 was incubated with buffer alone (lane 2) or with lysates from bacteria expressing GST (lane 3) or GST-CYPA (lane 4). Processing of samples is as in FIG. 4A. Lane 1 shows input bacterial lysate expressing p24.

The ability of bacterially expressed HIV-1 IN to bind to the GST-CyP proteins was tested. IN showed very faint binding to the GST-CyP proteins (FIG. 4B, lane 4), but this binding was below the background level of IN binding to G beads alone (FIG. 4B, lane 2). Also, this binding was insignificant when compared with the binding of IN to GIBP (FIG. 4B, lane 5), a GST fusion protein with a new host protein identified in the GAL4 two hybrid system that binds to HIV-1 IN (G.V.K. and S.P.G., unpublished data). Using the same in vitro binding assay, the ability of fragments of Pr55$^{gag}$ to bind to the GST-CyP proteins was tested. Two Gag proteins encoded by plasmids with terminators at positions 1906 and 1787 (with respect to the 5' end of the DNA provirus) bound specifically to the GST-CyP proteins. The bacterially expressed HIV-1 CA (p24) was also capable of binding specifically (FIG. 4C). Thus, using the in vitro binding assay to map the gag sequences necessary for binding to CyP, results consistent with those obtained in the yeast two hybrid system were obtained. Two Gag protein, Pr55$^{gag}$ and p24, are capable of binding to the CyP proteins.

Pr55$^{gag}$-CyP Binding Persists under Conditions of High Salt and Detergent The effect of salt and detergent on the recovery of Gag by the GST-CyP proteins was examined. The substitution of EDTA for $Mg^{2+}$ and $Ca^{2+}$ in the incubation buffer caused a 2-fold decrease in binding (compare lanes 2 and 3 in FIG. 5A). The Pr55$^{gag}$-GST-CyPA interaction was inhibited by increases of salt in the binding buffer, but was still easily detected in the presence of 200 mM KCI (FIG. 5A, lane 4).

Figure 5A:
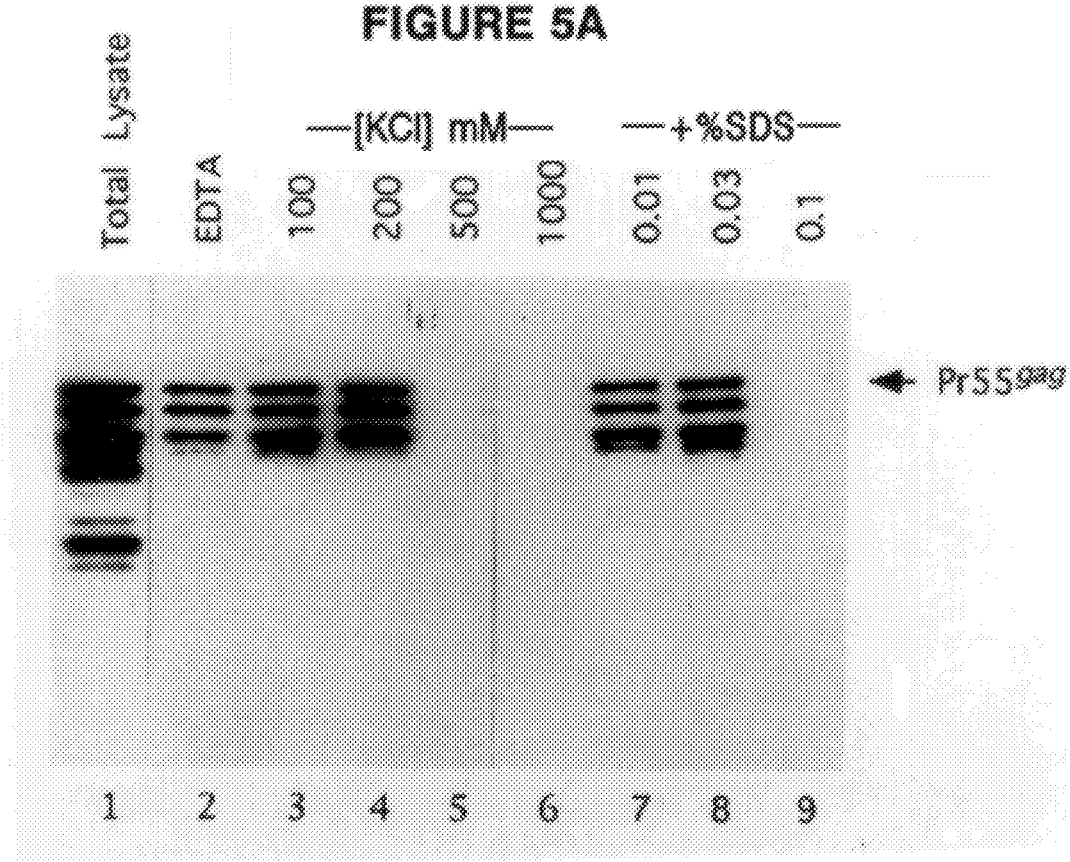
FIG. 5A and FIG. 5B. Pr55$^{gag}$ Binds to CyPs under Conditions of High Salt and Detergent. Lysate from bacteria expressing Pr55$^{gag}$ was incubated with GST-CyPA (FIG. 5A, lanes 2–9) or GST-CyPB (FIG. 5B, lanes 1–5). Binding experiments were performed as in FIG. 4A except that buffer conditions were changed. In lane 2 of FIG. 6A, 5 mM EDTA was substituted for CaCl$_2$ and MgCl$_2$. In lanes 3–6 of FIG. 5A and lanes 1–3 of FIG. 5B, the KCl concentration was varied as indicated. In addition to the 0.5% Nonidet P-40 present in the binding buffer, additional detergent (SDS) was added as shown in lanes 7–9 of FIG. 5A and lanes 4 and 5 of FIG. 5B. G beads were added and then washed three times with the indicated buffer. Samples were subjected to SDS-PAGE and Western blotting with mouse anti-p24 monoclonal antibody and peroxidase-linked sheep anti-mouse immunoglobulin. Input bacterial lysate expressing Pr55$^{gag}$ is shown in lane 1 of FIG. 5A and lane 6 of FIG. 5B.
Figure 5B:
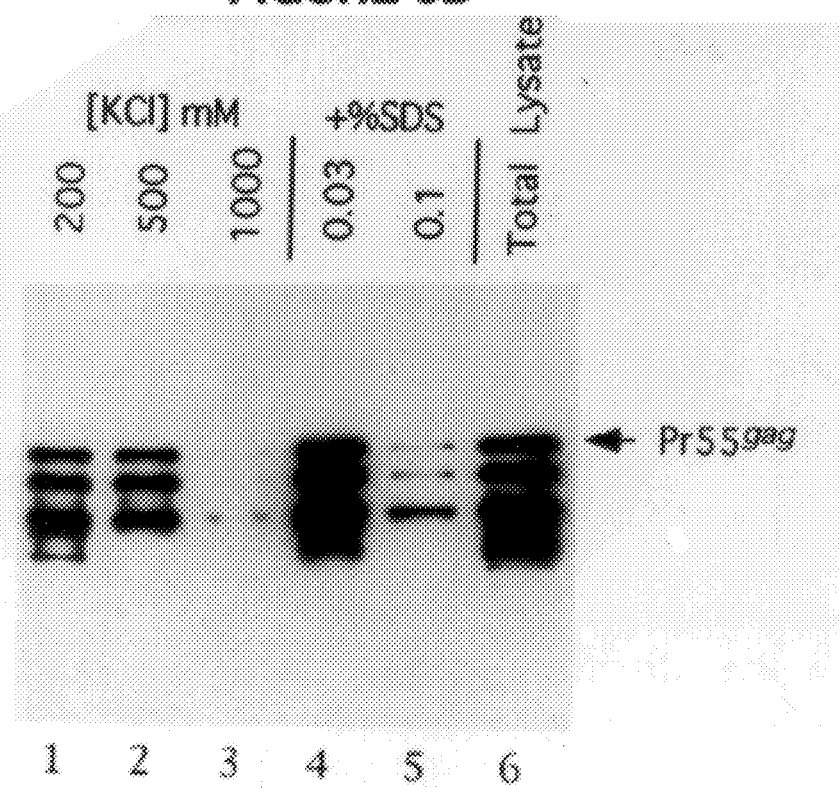

Binding was still apparent after the addition of 0.03% SDS (FIG. 5A, lane 8). With GST-CyPB there was detectable Pr55$^{gag}$ bound with as much as 1000 mM KCl (FIG. 5B, lane 3) or 0.1% SDS (FIG. 5B, lane 5). The interaction of Pr55$^{gag}$ with the GST-CyP proteins is of a respectable strength, but that the binding to GST-CYPB is more resistant to disruption by both salt and ionic detergents than that of GST-CYPA.

CsA Inhibits the Pr55$^{gag}$-Cyp Interaction

Figures 6A, 6B:
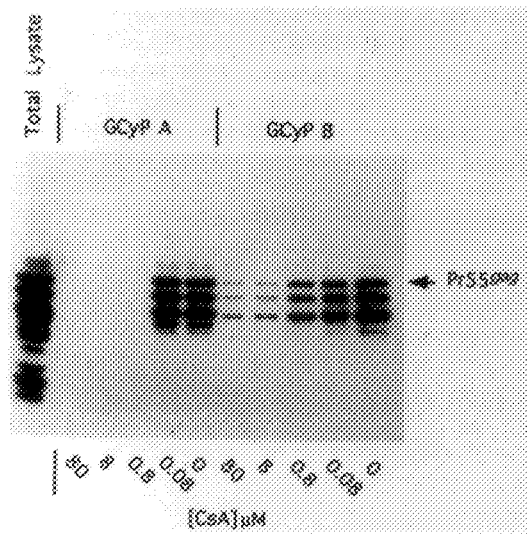
FIG. 6A. CsA Blocks Binding of Pr55$^{gag}$ to CyPs. GST-CyPA and GST-CyPB were preincubated with CsA at the concentrations indicated. Bacterial lysate containing Pr55$^{gag}$ was added and binding reactions were carried out as in FIG. 4A. G beads were added. Adsorbed proteins were washed three times and subjected to SDS-PAGE and Western blotting with mouse anti-p24 monoclonal antibody and peroxidase-linked sheep anti-mouse immunoglobulin.
FIG. 6B. This experiment was performed as in FIG. 6A using GST-CyPA with CsA concentrations as indicated.

The CyPs are the intracellular targets of the immunosuppressive drug CsA and are known to bind with a dissociation constant of roughly 6×10$^{-9}$ mol/l (Liu et al., 1992), though values in the range of 200 to 2×10$^{-9}$ have been reported (Sigal and Dumont, 1992). To determine whether CsA would affect the Pr55$^{gag}$-CyP interaction, the GST-CyP proteins with CsA prior to the addition of Pr55$^{gag}$ protein were incubated. Pr55$^{gag}$ binding to either GST-CYPA or GST-CyPB protein was inhibited by CsA (FIG. 6A). Titration of CsA showed that the concentrations of CsA required for inhibition of Pr55$^{gag}$-CyP binding were different for the two GST-CYP proteins. In these experiments it was estimate that the concentration of the Pr55$^{gag}$ was roughly 0.2 $\mu$M and that of GST-CyP was roughly 0.8 $\mu$M. For GST-CyPA, the slope of the Pr55$^{gag}$ binding inhibition curve was very steep (FIGS. 6A and 6B), such that Pr55$^{gag}$ binding was not affected at 0.4 $\mu$M CsA but was completely disrupted by 0.8 $\mu$M, close to the concentration of the GST-CyPA. Surprisingly, the same curve was not seen with GST-CyPB; there was a gradual inhibition of binding seen from 0.08–8 $\mu$M CsA, but even at 80 $\mu$M there was still detectable Pr55$^{gag}$ bound. Control experiments showed that CsA had no effect on the p32 (IN) interaction with GIBP. CsA specifically disrupts the interaction of Pr55$^{gag}$ with GST-CyP proteins. Either the binding sites overlap or binding of CsA induces conformational changes that prevent binding of Pr55$^{gag}$. CsA was less effective at disruption of the CyPB interaction than the CyPA interaction.

Pr55$^{gag}$-Cyp Complexes Do Not Bind Calcineurin

The Ca$^{2+}$-calmodulin-dependent protein phosphatase calcineurin (CN) is an important enzyme in the signaling pathways that lead to interleukin-2 release following T lymphocyte activation (Clipstone and Crabtree, 1992). A complex consisting of CyP protein and CsA has been shown to bind to and inhibit the activity of CN (Liu et al., 1991, 1992) and thus to disrupt the process of T cell activation. Neither CyP protein nor CsA is capable of binding to CN independently. Since infection with HIV-1 disrupts T cell function and number (Fauci, 1988), the complex of GST-CyP proteins with Pr55$^{gag}$ could bind to CN was examined.

Figure 7A:
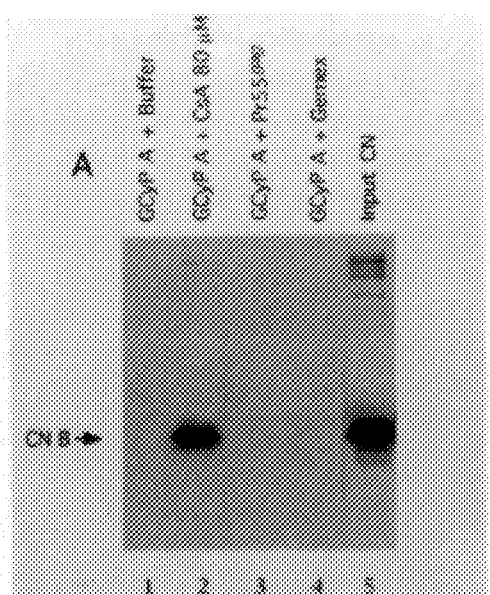
FIG. 7A and FIG. 7B. CN Does Not Bind Gag-CyP Complexes.
Figure 7B:
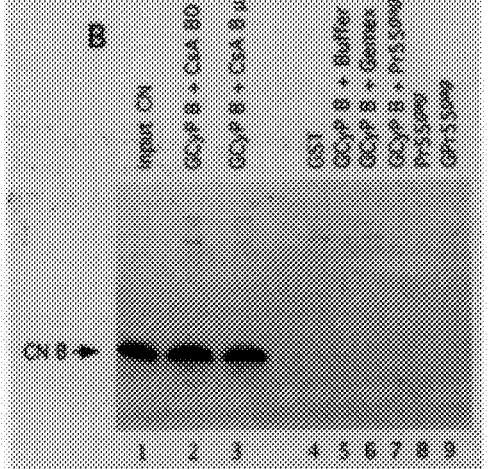
Figure 7C:
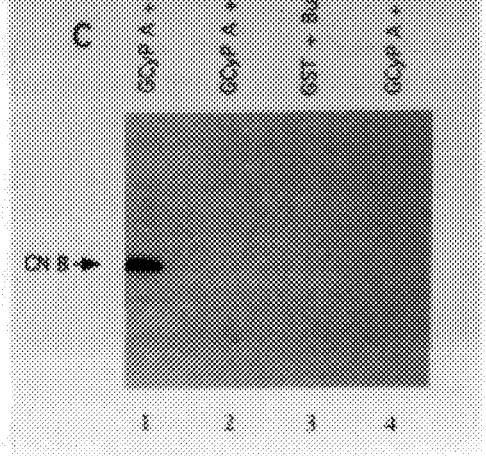
FIG. 7C. Bacterial lysates containing GST-CyPA (lanes 1, 2 and 4) or GST (lane 3) were mixed with buffer (lanes 2 and 3), CsA (lane 1), or p24-containing bacterial lysate (lane 4). G beads were added, washed twice, and incubated in buffer containing CN (0.1 μM) and calmodulin (0.5 μM). G beads were washed three times, and bound protein was subjected to SDS-PAGE and Western blotting with monoclonal anti-CN β subunit antibody.

Detection of the binding of CN by the complex of GST-CyPA plus CsA was first demonstrated (FIG. 7A, lane 2; FIG. 7B, lanes 2 and 3; FIG. 7C, lane 1). CN was detected with as little as 0.08 $\mu$M CsA added to the reactions. As expected, GST-CyPA alone does not bind CN (FIG. 7A, lane 1; FIG. 7B, lane 5; FIG. 7C, lane 2). The complex of GST-CyPA (FIG. 7A, lane 3) or GST-CyPB (FIG. 7B, lane 7) plus Pr55$^{gag}$ was not capable of binding detectable quantities of CN. The same result was obtained in multiple experiments, including some in which the GST-CyP proteins were incubated with milligram quantities of Pr55$^{gag}$ (FIG. 7B, lane 7); the Pr55$^{gag}$ concentrations in these experiments were at least 10-fold greater than the CsA concentrations necessary to detect binding of CN. There was no factor present in the bacterial lysates containing Pr55$^{gag}$ that inhibited CsA-GST-CyP from binding CN. The binding of CN to a complex of GST-CyP and p24 was not seen (FIG. 7C). Thus, the complex of Pr55$^{gag}$ or p24 with either of the CyP proteins was capable of binding to CN was not observed.

The two hybrid system was used to screen for cDNAs encoding proteins that interact with Pr55$^{gag}$ has revealed a significant interaction with the class of proteins known as CyPs. Colonies (5×10$^5$) were initially screened, and two clones were identified, both of which express GAL4-CyP fusion proteins. Subsequent screening resulted in the recovery of three additional CyP clones. This binding is readily demonstrated in vitro, persists under conditions of high salt and detergent (FIG. 5), and is inhibited by CsA at concentrations that suggest that the binding of CsA titrates the binding sites on the CyPs for the Pr55$^{gag}$ (FIG. 6). CsA is more effective at disruption of the Gag-CyPA interaction than the Gag-CyPB interaction. These results extend the proteins identified with the two hybrid system from those that interact with transcriptional regulators (Chevray and Nathans, 1992; Chien et al., 1991; Hardy et al., 1992) and protein kinases (Yang et al., 1992) to include proteins that interact with a viral structural protein.

The nine false positive clones identified in the assay all encode proteins with RNA binding activity (Table 1). Why such clones score positive, a similar array of genes encoding RNA-binding proteins in screens with other retroviral Gags have been recovered. These clones were identified as false positive because they had activity against the parent GAL4 DNA-binding domain expression plasmid without Gag sequences. Though they were active against a lexA-Pr55$^{gag}$ expression plasmid, they did not interact with the parent lexA expression plasmid and would have been falsely identified as true positives if the library had only been screened with the lexA two hybrid system.

Since at least two different CyPs bind to Gag protein, the conserved core that is common between the different CyPs (Stamnes et al., 1992) most likely confers the ability to bind to the Gag protein. From the data it is not possible to conclude whether one CyP is more important than another in terms of binding to Gag. A member(s) of the CyP family other than the two that were cloned could also be a relevant partner(s) for interaction with Gag. Knowledge of the cellular compartment in which the Gag-CyP interaction takes place would provide an important clue as to which CyP is the relevant partner for Gag protein.

The central portion of Pr55$^{gag}$ (FIG. 2) and the separate p24 (CA) (FIG. 4C) are capable of binding to CyPs. Therefore, either Pr55$^{gag}$ or p24 may be the biologically relevant partner in the Gag-CyP interaction. Since Pr55$^{gag}$ is present in the cell at the time of virion particle assembly and p24 is probably only present in the cell acutely following infection, it is possible that the Gag-CyP takes place at either stage of the retroviral life cycle.

There is no obvious structural similarity between Pr55$^{gag}$ and CsA that would suggest a binding motif. The CsA-CyP is probably monomeric in solution (Theriault et al., 1993), but may form a complex decameric structure consisting of two pentamers at high concentrations (Pflugl et al. 1993). Competition data between Pr55$^{gag}$ and CsA for binding to CyPA have a very steep curve. Pr55$^{gag}$ is capable of forming homomultimers (Luban et al., 1992), the curve may reflect the need for the complete titration of all available CsA-binding sites on the CyPA before displacement of a large oligomeric Gag complex occurs. Alternatively, it may reflect a cooperativity of Gag binding within the Gag-CyP complex that is disrupted by CsA.

Significance of the Gag-CyP Interaction for the Retroviral Life Cycle

Although there is a tremendous amount of information about the CyPs, a class of proteins found throughout nature (Heitman et al., 1992; Stamnes et al., 1992), all the functions of the CyPs are not known with any certainty. The CyPs possess a conserved core sequence with variable amino and carboxyl termini that direct them to different cellular compartments. These proteins possess peptidyl-prolyl cis-trans isomerase activity and may have a role in directing the proper folding of cellular proteins. CsA, a drug that disrupts the CyP isomerase activity, blocks collagen triple helix assembly in fibroblasts (Steinmann et al., 1991) and prevents formation of the correct disulfide-bonded form of transferrin in HepG2 cells (Lodish and Kong, 1991). CyPs may also play a role in directing proteins to the proper locations within cells. Transit from the endoplasmic reticulum of specific isoforms of rhodopsin is blocked in Drosophila by mutations in the ninaA gene, a member of the CyP family (Colley et al., 1991; Stamnes et al., 1991). Thus, the CyP proteins may be important for the proper folding of Gag proteins or for targeting them to the cell membrane. Preliminary experiments examining the effect of CsA on HIV-1 replication have revealed that the drug may block infection if present at the time of infection (Wainberg et al., 1988) or decrease the yield of infectious particles released by the cells (Karpas et al., 1992). These effects are confounded by the effects of the drug on the activation state of the T cell and on transcription from the viral promoter. Some of these issues might by clarified by studying the effect on viral replication of compounds such as MeAla-CsA (Sigal et al., 1991) that bind to CyPs but do not suppress T cell activation.

The Gag-CyP interaction may not be important for other retroviruses, since the Gag polyproteins of MPMV and MOMLV did not bind to the CyPs (Table 2). Interestingly, the Gag polyprotein of SIV-1, an immunosuppressive retrovirus closely related to HIV-1, had activity against CyPB.

Relevance of Gag-CVP Interaction for the Pathogenesis of AIDS

As part of a complex with CyP, CsA inactivates the phosphatase activity of CN and disrupts pathways that lead to transcriptional activation in T cells (McKeon, 1991; Schreiber and Crabtree, 1992). It may be postulated that Gag might inhibit T cell responses via a similar mechanism. HIV-1 Gag protein exhibits CsA-inhibitable binding to CyP proteins was not demonstrated and the Gag-CyP complex was capable of binding to CN was not demonstrated (FIG. 7). Thus, Gag protein does not seem directly to mimic CsA in its effect on the T cell activation pathway. The relationship between Gag protein and CsA may be analogous to that of rapamycin and FK506. Rapamycin and FK506 are immunosuppressive compounds that inhibit T cell responses via an interaction with the same immunophilin, FKBP. As with the CsA-CyP complex, the FK506-FKBP complex is capable of binding to and inhibiting the phosphatase activity of CN (Liu et al., 1991, 1992), thereby blocking pathways of T cell activation. Rapamycin competes with FK506 for binding to FKBP (Bierer et al., 1990), but the complex of rapamycin-FSBP is not capable of binding CN. Perhaps the rapamycin-FKBP complex binds to a phosphatase as yet unidentified (Schreiber, 1992) that is also a target of the Gag-CyP complex.

It has been suggested that there is a native ligand for CyP that regulates the activation state of the T cell (Schreiber and Crabtree, 1992). A 77 kd CyP-binding protein has been identified that might serve this function (Friedman and Weissman, 1991). Rather than promoting binding to a regulatory enzyme like CN, Gag protein might affect the host cell by disrupting the binding of CyPs with a native ligand.

Several HIV-1 genes have been associated with the cytotoxic or immunosuppressive effects of the virus. HIV-1 protease has been shown to be active in the cytoplasm of infected cells (Kaplan and Swanstrom, 1991) and to be toxic in cell culture (Krausslich et al., 1993). This might be because intermediate filaments serve as protease substrates in cells (Shoeman et al., 1990). Purified Tat protein, as well as synthetic Tat peptide, inhibits antigen-stimulated lymphocyte proliferation (Viscidi et al., 1989). There are conflicting reports about the ability of the nef gene product to block the induction of interleukin-2 transcription (Luria et al., 1991; Schwartz et al., 1992). The env gene product gp120 has been implicated in the immunopathogenesis of HIV-1 by several mechanisms. Env protein is cytotoxic via syncytia formation and may serve as a cell surface signal for the immune system to eliminate HIV-infected cells (Pantaleo et al., 1993). There are also conflicting reports about the role of env gene products in immunosuppression; purified gp120 may (Kornfeld et al., 1988; Weinhold et al. 1989) or may not (Horak et al., 1990; Kaufmann et al., 1992) affect T cell activation, and gp120-CD4 interactions may or may not be necessary or the activation-induced cell death (apoptosis) that is hypothesized to play a role in the $CD4^+$ T cell destruction seen in AIDS patients (Groux et al., 1992; Laurent-Crawford et al., 1991; Meynaard et al., 1992; Terai et al., 1991). The apoptosis observed with HIV-1-infected T cells can be blocked by CsA (Groux et al., 1992) and might in fact be related to the Gag-CyP interaction.

Antibodies and Proteins

Murine monoclonal antibody against HIV-1 p24 was obtained from Biotech Research Labs, Incorporated, Billerica, Mass. Murine monoclonal antibody against HIV-1 p32 (IN) was a gift from Dr. Dag Helland (University of Bergen, Bergen, Norway). Horseradish peroxidase-linked sheep anti-mouse immunoglobulin antibody was obtained from Amersham International (England). Bovine brain CN (phosphatase 2B) and calmodulin and murine monoclonal antibody against the CN β subunit were obtained from Upstate Biotechnology, Incorporated, Lake Placid, N.Y. CsA (Sandimmune I.V.) was obtained from Sandoz Pharmaceuticals Corporation, East Hanover, N.J.

Plasmids and cDNA Library

The construction of plasmids pGAL4ACX-HG, pGAL4DB-HG, and pGAL4DB-MG was previously described (Luban et al., 1992), as was the construction of plasmid pT7HG(pro⁻) (Luban and Goff, 1991). pGEMEX-1 was obtained from Promega Corporation, Madison, Wis. pSH2-1 is a yeast shuttle vector that expresses fusion proteins with lexA amino acids 1-87 under control of the ADH1 promoter (Hanes and Brent, 1989). PLAG was constructed by inserting the HIV-1 $Pr55^{gag}$ containing BamHI-Sal1 fragment from pGAL4ACX-HG into pSH2-1.

All recombinant DNA methods were performed according to standard protocols (Sambrook et al., 1989). pT7p24 was constructed from the product of a polymerase chain reaction using pT7HG(pro⁻) as template, with the mutagenic oligos 5'-CGCGCATATGCCTATAGTGCAGAACATCCAGGG-3' (Seq. ID No. 7) and 5'-GCGCGTCGACTTAAACTCTTGCCTTATGGCC-3'

(Seq. ID No. 8). This product was digested with NdeI and SalI and ligated to a modified version of pGEMEX-1 (Luban and Goff, 1991) digested with the same enzymes.

The constructions of the panel of linker insertion mutations in the HIV-1 gag coding sequence has been described (Luban et al., 1993). These mutant gag sequences were used to replace wild-type coding sequences in pGAL4DB-HG, using standard procedures (Sambrook et al., 1989). The construction of plasmids pGAL4DB-MPG, pGAL4DB-SG, and pGAL4DB-IN and of the various $Pr55^{gag}$ deletion mutations is described elsewhere (G.V.K. and S.P.G., submitted; J.L. and S.P.G., unpublished data).

pGEX-2T (Smith and Johnson, 1988) was obtained from Pharmacia LKB Biotechnology, Piscataway, N.J. BamHI and BgI fragments containing the 4cDNA library inserts from clones 2.1 and 4.1 were subcloned into PGEX-2T cleaved with BamH, and the resulting GST-CyP expression plasmids were called pGCyPA and pGCyPB, respectively.

PGADNOT was constructed from pGAL4ACX-HG (Luban et al., 1992) to facilitate subcloning of cDNA library inserts. The parental pGAL4ACX-HG DNA was digested with BamH plus Sal, and the resulting 8.4 kb fragment was ligated to two annealed oligonucleotide adaptors (5'-GATCCGCGGCCGCCATATGG-3' (Seq. ID No. 9) and 5'-TCGACCATATGGCGGCCGCG-3' (Seq. ID No. 10) using standard methods (Sambrook et al., 1989), yielding pGADNOT. This DNA was digested with Not plus Sal and ligated to Not-XhoI fragments excised from a CDNA library constructed from HL-60 RNA (Stratagene®, La Jolla, Calif.). Pools of more than 150,000 bacterial colonies were collected and used to prepare plasmid DNA.

Screening of CDNA Library

Yeast were transformed using the lithium-acetate method (Becker and Guarente, 1991). To screen the HL-60 cDNA library, *S. cerevisiae* GGY1::171 (gal4, gal80, ura3, his3, leu2) (Gill and Ptashne, 1987), carrying a Gal1-lacZ fusion gene integrated into the chromosome, was sequentially transformed with pGAL4DB-HG followed by transformation with DNA from an individual pGADNOT-HL-60 cDNA pool, and double transformants were selected for histidine and leucine prototrophy. β-Gal activity was assayed on nitrocellulose filter replicas of yeast transformants (Breedon and Nasmyth, 1985). Filters were placed at −70° C. for 20 minutes and incubated for 8 hours in buffer containing X-Gal. If transformants expressed β-Gal activity, the X-Gal was cleaved and only replicas turned blue. Individual colonies were isolated, replanted, and retested sequentially for β-gal activity three times. Plasmid DNA was isolated from the blue colonies (Strathern and Higgins, 1991) and used to transform *Escherichia coli* DH5α to ampicillin resistance by electroporation. Bacteria transformed with pGADNOT-cDNA plasmids were identified by restriction digest patterns, and the isolated plasmids were then retested in yeast for β-gal activity.

For testing pGADNOT-cDNA library clones against pLAG, *S. cerevisiae* was utilized CYT 10-5d (gal4, gal80, ade2, his3, leu2, trp1, ura3) that has lexA dimer-binding sites upstream of the transcription start site of an integrated copy of GAL1-lacZ (a gift from Stanley Fields and Rolf Sternglanz, State University of New York at Stony Brook, Stony Brook, N.Y.).

Sequence Analysis of pGADNOT-cDNA Clones

Sequences at the 5' and 3' ends of the cDNA inserts were obtained by dideoxy sequencing using oligonucleotide primers from GAL4 sequences 5'-GATGATGAAGATACC-3' (Seq. ID No. 11) and 5'-GGTGCACGATGCACAG-3' (Seq. ID No. 12) annealed to GAL4 sequences.

Expression of Protein in Bacteria

GST-CyP fusion protein expression plasmids were grown in *E. coli* strain DH5α. Plasmids expressing native $Pr55^{gag}$, p24, and p32 (IN) proteins from the T7 promoter were grown in JB-DE3, a long mutant stain containing the T7 polymerase under the control of the lac4 mutant UV5 promoter (Luban and Goff, 1991). Protein was induced from bacterial expression plasmids with isopropyl-β-D-thiogalactopyranoside according to standard methods (Sambrook et al., 1989). Bacteria were pelleted 3 hours after induction, washed in TEK buffer (20 mM Tris-HCl [pH 7.5], 1 mM EDTA, and 100 mM KCl), and resuspended in lysis buffer (10 mM Tris-HCl [pH 7.5], KCl 100 mM, 1 mM EDTA, 5 mM dithiothreitol, 1.0 mM phenylmethylsulfonyl fluoride, and 0.5% Nonidet P-40). The suspended bacteria were frozen and thawed six times and sonicated on ice for 30 seconds with a Branson Sonifier 250 (Branson Sonic Power Company, Danbury, Conn.), at an output setting of 1 with a 30% duty cycle. Insoluble material was pelleted at 90° K. for 10 minutes in a Beckman TL-100 ultracentrifuge. Total protein concentration in the supernatant was determined by the Bradford dye-binding procedure (Bio-Rad Laboratories, Hercules, Calif.). Supernatants were adjusted to 20% glycerol and stored at −70° C.

Adsorption of $Pr55^{gag}$ Using GST-CYP and G Beads

G beads (Sigma® Chemical Corporation, St. Louis, Mo.) were swollen overnight at 4° C. in TEK buffer, washed three times in TEK buffer with 0.5% powdered milk, and stored at 4° C. in binding buffer (20 mM Tris-HCl [pH 7.5], 100 mM CK1, 2 mM $CaCl_2$, 2 mM $MgCl_2$, 5 mM dithiothreitol, 0.5% Nonidet P-40, 0.5 mM phenylmethylsolfonyl fluoride, and 5% glycerol). Typical binding reactions used crude bacterial lysates in a total volume of 200 μl of binding buffer containing approximately 2 μg of $Pr55^{gag}$ (approximately 0.2 μM) and 2 μg of GST-CyP (approximately 0.2 μM). After incubation at 4° C. on a nutator (Becton-Dickinson, Parsippany, N.J.), 25 μl of 50% (v/v) G beads in binding buffer was added, and incubation was continued for another 30 minutes. The G beads were collected with a 5 s pulse in a microfuge and washed three times with 400 μl of binding buffer. Washed G beads were resuspended in 25 μl of 2×SDS sample buffer (Sambrook et al., 1989), heated in boiling water for 5 minutes, and pelleted in a microfuge. The supernatant (5 μl) was subjected to SDS-polyacrylamide gel electrophoresis (SDS-PAGE). Gels were either stained with Coomassie blue or processed for Western blot analysis. For CsA competition experiments, the GST-CyP protein was incubated for 5 minutes with CsA in binding buffer, prior to the addition of the bacterial lysate containing $Pr55^{gag}$.

Adsorption of CN with GST-CYP Protein and G Beads

CN adsorption experiments were performed two ways. In some experiments, GST-CyP protein was incubated as described above with either $Pr55^{gag}$ or CsA but with the addition of 2 μg of CN (0.1 μM) and 2 μg of calmodulin (0.5 μM). G beads were added, incubated, and processed normally. In other experiments, GST-CyP protein was first adsorbed to G beads in binding buffer for 1 hour at 4° C. The G beads were then washed two times and incubated with CsA or bacterial lysates containing Pr55$^{gag}$. In some of these experiments, bacterial cultures were scaled up so that GST-CYP-G bead complexes were incubated with 1–2 mg of Pr55$^{gag}$. Beads were incubated another hour at 4° C. and washed twice. Binding buffer with CN and calmodulin was added, and the mixture was incubated for 1 hour. The G beads were washed and subjected to SDS-PAGE and Western blot analysis as before.

Western Blot Analysis of Pr55$^{gag}$, p32 (IN), and CN

Proteins were electrotransferred to nitrocellulose membranes with the Bio-Rad® mini-blotting apparatus (Bio-Rad Laboratories, Hercules, Calif.). Blots were incubated with either the mouse monoclonal anti-Pr55$^{gag}$, anti-p32 (IN), or anti-CN a subunit antibodies, followed by horseradish peroxidase-linked sheep anti-mouse immunoglobulin. Antibody binding was detected with ECL Western blotting detection reagents (Amersham, England).

REFERENCES

1. Becker, D., and Guarente, L. (1991) High-Efficiency transformation of yeast by electroporation. In Guide to Yeast Genetics and Molecular Biology, C. Guthrie and G. R. Fink, eds. (San Diego, Calif.; Academic Press), pp. 182–186.
2. Bierer, B., Mattila, P., Standaert, R., Herzenberg, L., Burakoff, S., Crabtree, G., and Schreiber, S. (1990) Two distinct signal transmission pathways in T lymphocytes are inhibited by complexes formed between an immunophilin and either FK506 or rapamycin. Proc. Natl. Acd. Sci. USA, 87:9231–9235.
3. Bowerman, B., Brown, P. O., Bishop, J. M., and Varmus, H. E. (1989) A nucleoprotein complex mediates the integration of retroviral DNA. Genes Dev., 3:469–478.
4. Breedon, L., and Nasmyth, K. (1985) Regulation of HO gene. Cold Spring Harbor Symp. Quant. Bio., 50:643–650.
5. Chevray, P., and Nathans, D. (1992) Protein interaction cloning in yeast: identification of mammalian proteins that react with the leucine zipper of Jun. Prac. Natl. Acad. Sci. USA, 89:5789–5793.
6. Chien, C.-T., Bartel, P. L., Sternglanz, R., and Fields, S. (1991) The two-hybrid system: a method to identify and clone genes for proteins that interact with a protein of interest. Proc. Natl. Acad. Sci. USA, 88:9578–9582.
7. Clipstone, N., and Crabtree, G. (1992) Identification of calcineurin as a key signalling enzyme in T-lymphocyte activation. Nature, 357:695–697.
8. Colley, N. J., Baker, E. K., Stamnes, M. A., and Zuker, C. S. (1991) The cyclophilin homolog ninaA is required in the secretory pathway. Cell, 67:255–263.
9. DesGroseillers, L., and Jolicoeur, P. (1983) Physical mapping of the Fv-1 tropism host range determinant of BALB/c murine leukemia viruses. J. Virol., 48:685–696.
10. Fauci, A. (1988) The human immunodeficiency virus: infectivity and mechanisms of pathogenesis. Science, 239:617–622.
11. Fields, S., and Song, O. (1989) A novel genetic system to detect protein-protein interactions. Nature, 340:245–246.
12. Fields, S., and Song, O.-K. (1994). System To Detect Protein-Protein Interactions. U.S. Pat. No. 5,283,173.
13. Friedman, J., and Wiessman, I. (1991) Two cytoplasmic candidates for immunophilin action are revealed by affinity for a new cyclophilin: one in the presence and one in the absence of CsA. Cell, 66:799–805.
14. Gill, G., and Ptashne, M. (1987) Mutants in GAL4 protein altered in an activation function. Cell, 51:121–126.
15. Gottlinger, H. G., Sodroski, J. G., and Haseltine, W. A. (1989) Role of capsid precursor processing and myristoylation in morphogenesis and infectivity of human immunodeficiency virus type 1. Proc. Natl. Acad. Sci. USA, 86:5781–5785.
16. Groux, H., Torpier, G., Monte, D., Mouton, Y., Capron, A., and Ameisen, J. (1992) Activation-induced death by apoptosis in CD4$^+$ T cells from human immunodeficiency virus-infected asymptomatic individuals. J. Exp. Med., 175:331–340.
17. Handschumacher, R., Harding, M., Rice, J., and Drugge, R. (1984) Cyclophilin: a specific cytosolic binding protein for cyclosporin A. Science, 226:544–547.
18. Hanes, S. D., and Brent, R. (1989) DNA specificity of the bicoid activator protein is determined by homeodomain recognition helix residue 9. Cell, 57:1275–1283.
19. Hardy, C. F. J., Sussel, L., and Shore, D. (1992) A RAP1-interacting protein involved in transcriptional silencing and telomere length regulation. Genes Dev., 6:801–814.
20. Heitman, J., Movva, N. R., and Hall, M. N. (1992) Proline isomerases at the crossroads of protein folding, signal transduction, a dn immunosuppression. New Biol., 4:448–460.
21. Hopkins, N., Schindler, J., and Hynes, R. (1977) Six NB-tropic murine leukemia viruses derived from a B-tropic virus of BALB/c have altered P30. J. Virol., 21:309–318.
22. Horak, I. D., Popovic, M., Horak, E. M., Lucas, P. J., Gress, R. E., June, C. H., and Bolen, J. B. (1990) No T-cell tyrosine protein kinase signalling or calcium mobilization after CD4 association with HIV-1 or HIV-1 gp120. Nature, 348:557–560.
23. Hsu, H., Schwartzberg, P., and Goff, S. (1985) Point mutation in the p30 domain of the gag gene of Moloney murine leukemia virus. Virology, 142:211–214.
24. Kaelin, W. G., Jr., Pallas, D. C., DeCaprio, J. A., Kaye, F. J., and Livingston, D. M. (1991) Identification of cellular proteins that can interact specifically with the T/E1A-binding region of the retinoblastoma gene product. Cell, 64:521–532.
25. Kaplan, A., and Swanstrom, R. (1991) Human immunodeficiency virus type 1 Gag proteins are processed in two cellular compartments. Proc. Natl. Acad. Sci. USA, 88:4528–4532.
26. Karpas, A., Lowdell, M., Jacobson, S., and Hill, f. (1992) Inhibition of human immunodeficiency virus and growth of infected T cells by the immunosuppressive drugs cyclosporin A and FK506. Proc. Natl. Acad. Sci. USA, 89:8351–8355.
27. Kaufmann, R., Laroche, D., Buchner, K., Hucho, F., Rudd, C., Lindschau, C., Ludwig, P., Hoer, A., Oberdisse, E., Kopp, J., Korner, I.-J., and Repke, H. (1992) The HIV-1 surface protein gp120 has no effect on transmembrane signal transduction in T cells. J. Acquir. Immune Defic. Syndr., 15:760–770.
28. Kornfeld, H., Cruikshank, W. W., Pyle, S. W., Berman, J. S., and Center, D. M. (1988) Lymphocyte activation by HIV-1 envelope glycoprotein. Nature, 335:445–448.
29. Krausslich, H.-G., Ochsenbauer, C., Traenckner, A.-M., Mergener, K., Facke, M., Gelderblom, H., and Bosch, V. (1993) Analysis of protein expression and virus-like particle formation in mammalian cell lines stably expressing HIV-1 gag and env gene products with or without active HIV proteinase. Virology, 192:605–617.

30. Laurent-Crawford, A., Krust, B., Muller, S., Riviere, Y., Rey-Cuille, M.-A., Bechet, J.-M., Montagnier, L., and Hovanessian, A. (1991) The cytopathic effect of HIV is associated with apoptosis. *Virology*, 185:829–839.
31. Lilly, F., and Pincus, T. (1973) Genetic control of murine viral leukemogenesis. *Adv. Cancer. Res.*, 17:231–277.
32. Liu, J., Farmer, J. D., Jr., Lane, W. S., Friedman, J., Weissman, I., and Schreiber, S. L. (1991) Calcineurin is a common target of cyclophilin-cyclosporin A and FKBP-FK506 complexes. *Cell*, 66:807–815.
33. Liu, J., Albert, M., Wandless, T., Luan, S., Albert, D., Belshaw, P., Cohen, P., MacKintosh, C., Klee, C., and Schreiber, S. (1992) Inhibition of T cell signaling by immunophilin-ligand complexes correlates with loss of calcineurin phosphatase activity. *Biochemistry*, 31:3896–3901.
34. Lodish, H., and Kong, N. (1991) Cyclosporin A inhibits an initial step in folding of transferrin within the endoplasmic reticulum. *J. Biol. Chem.*, 266:14835–14838.
35. Luban, J., and Goff, S. (1991) Binding of human immunodeficiency virus type 1 (HIV-1) RNA to recombinant HIV-1 gag polyprotein. *J. Virol.*, 65:3203–3212.
36. Luban, J., Alin, K. B., Bossolt, K. L., Humaran, T., and Goff, S. P. (1992) Genetic assay for multimerization of retroviral gag polyproteins. *J. Virol.*, 66:5157–5160.
37. Luban, J., Lee, C., and Goff, S. (1993) Effect of linker insertion mutations in the human immunodeficiency virus type 1 (HIV-1) gyag gene on activation of viral protease expressed in bacteria. *J. Virol.*, in press.
38. Luria, S., Chambers, I., and Berg, P. (1991) Expression of the type 1 human immunodeficiency virus Nef protein in T cells prevents antigen receptor-mediated induction of interleukin 2 mRNA. *Proc. Natl. Acad. Sci. USA*, 88:5326–5330.
39. McKeon, F. (1991) When worlds collide: immunosuppressants meet protein phosphatases. *Cell*, 66:823–826.
40. Meyaard. L., Otto, S., Jonker, R., Mijnster, M., Keet, R., and Miedema, F. (1992) Programmed death of T cells in HIV-1 infection. *Science*, 257:217–219.
41. Pantaleo, G., Graziosi, C., and Fauci, A. (1993) The immunopathogenesis of human immunodeficiency virus infection. *N. Engl. J. Med.*, 328:327–335.
42. Pflugl, G., Kallen, J., Schirmer, T., Jansonius, J., Zurini, M., and Walkinshaw, M. (1993) X-ray structure of a decameric cyclophilin-cyclosporin crystal complex. *Nature*, 361:91–94.
43. Rein, A., McClure, M., Rice, N., Luftig, R., and Schultz, A. (1986) Myristylation site in Pr65$^{gag}$ is essential for virus particle formation by Moloney murine leukemia virus. *Proc. Natl. Acad. Sci. USA*, 83:7246–7250.
44. Rhee, S., and Hunter, E. (1987) Myristylation is required for intracellular transport but not for assembly of D-type retrovirus capsids. *J. Virol.* 61:1045–1053.
45. Sambrook, J., Fritsch, E. F., and Maniatis, T. (1989) Molecular Cloning: A Laboratory Manual, Second Edition (Cold Spring Harbor, N.Y.: Cold Spring Harbor Laboratory Press).
46. Schreiber, S. L. (1992) Immunophilin-sensitive protein phosphatase action in cell signaling pathways. *Cell*, 70:365–368.
47. Schreiber, S. L. and Crabtree, G. R. (1992) The mechanism of action of cyclosporin A and FK506. *Immunol. Today*, 13:136–142.
48. Schwartz, O., Arenzana-Seisdedos, F., Heard, J.-M., and Danos, O. (1992) Activation pathways and human immunodeficiency virus type 1 replication are not altered in CD4$^+$ T cells expressing the Nef protein. *AIDS Res. Hum. Retroviruses*, 8:545–551.
49. Shoeman, R., Honer, B., Stoller, T., Kesselmeier, C., Miedel, M., Traub, P., and Graves, M. (1990) Human immunodeficiency virus type 1 protease cleaves the intermediate filament proteins vimentin, desmin, and glial fibrillary acidic protein. *Proc. Natl. Acad. Sci. USA*, 87:6336–6340.
50. Sigal, H. H., and Dumont, F. J. (1992) Cyclosporin A, FK506, and rapamycin. *Annu. Rev. Immunol.*, 10:519–560.
51. Sigal, N. H., Dumont, F., Durette, P., Siekierka, J. J., Peterson, L., Rich, D. H., Dunlap, B. E., Staruch, M. J., Melino, M. R., Koprak, S. L., Williams, D., Witzel, B., and Pisano, J. M. (1991) Is cyclophilin involved in the immunosuppressive and nephrotoxic mechanism of action of cyclosporin A? *J. Exp. Med.*, 173:619–628.
52. Smith, D. B., and Johnson, K. S. (1988) Single-step purification of polypeptides expressed in *Escherichia coli* as fusions with glutathione S-transferase. *Gene*, 67:31–40.
53. Stamnes, M. A., Shieh, B.-H., Chuman, L., Harris, G. L., and Zuker, C. S. (1991) The cyclophilin homolog ninaA is a tissue-specific integral membrane protein required for the proper synthesis of a subset of Drosophila rhodopsins. *Cell*, 65:219–227.
54. Stamnes, M. A., Rutherford, S. L., and Zuker, C. S. (1992) Cyclophilins: a new family of proteins involved in intracellular folding. *Trends Cell. Biol.*, 2:272–276.
55. Steinmann, B., Bruckner, P., and Superti-Furga, A. (1991) Cyclosporin A slows collagen triple-helix formation in vivo: indirect evidence for a physiologic role of peptidyl-prolylcis-trans-isomerase. *J. Biol. Chem.*, 266:1299–1303.
56. Strambio-deCastillia, C., and Hunter, E. (1992) Mutational analysis of the major homology region of Mason-Pfizer monkey virus by use of saturation mutagenesis. *J. Virol.*, 66:7021–7032.
57. Strathern, J. N., and Higgins, D. R. (1991) Recovery of plasmids from yeast into *Escherichia coli*: shuttle vectors. In Guide to Yeast Genetics and Molecular Biology, C. Guthrie and G. R. Fink, eds. (San Diego, Calif.: Academic Press), pp. 319–328.
58. Terai, C., Kornbluth, R., Pauza, C., Richman, D., and Carson, D. (1991) Apoptosis as a mechanism of cell death in cultured T lymphoblasts acutely infected with HIV-1. *J. Clin. Invest.*, 87:1710–1715.
59. Theriault, Y., Logan, T. M., Meadows, R., Yu, L., Olejniczak, E. T., Holzman, T. F., Simmer, R. L., and Fesik, S. W. (1993) Solution structure of the cyclosporin A/cyclophilin complex by NMR. *Nature*, 361:88–91.
60. Viscidi, R., Mayur, K., Lederman, H., and Frankel, A., (1989) Inhibition of antigen-induced lymphocyte proliferation by Tat protein from HIV-1. *Science*, 246:1606–1608.
61. Wainberg, M., Dascal, A., Blain, N., Fitz-Gibbon, L., Boulerice, F., Numazaki, K., and Tremblay, M. (1988) The effect of cyclosporine A on infection of susceptible cells by human immunodeficiency virus type 1. *Blood*, 72:1904–1910.
62. Weinhold, K., Lyerly, H., Stanley, S., Austin, A., Matthews, T., and Bolognesi, D. (1989) HIV-1 gp120-mediated immune suppression and lymphocyte destruction in the absence of viral infection. *J. Immunol.*, 142:3091–3097.
63. Weiss, R., Teich, N., Varmus, H., and Coffin, J. (1984) RNA Tumor Viruses (Cold Spring Harbor, N.J.: Cold Spring Harbor Laboratory Press).
64. Wills, J. W., and Craven, R. C. (1991) Form, function, and use of retroviral Gag proteins. *AIDS*, 6:639–654.

65. Yang, X., Hubbard, J., and Carlson, M. (1992) A protein kinase substrate identified by the two-hybrid system. *Science,* 257:680–682.

66. Zervos, A. S., Gyuris, J., and Brent, R. (1993) Mxi1, a protein that specifically interacts with Max to bind Myc-Max recognition sites. *Cell,* 72:223–232.

What is claimed is:

1. A method for identifying compounds capable of interfering with the formation of a complex between an HIV-1 Gag protein and a cyclophilin (CyP), which comprises the following steps:

a) producing a CyP affinity fusion protein;

b) pre-incubating a compound with the CyP affinity fusion protein of step (a);

c) adding an HIV-1 Gag protein to the incubate of step (b) under conditions which permit Gag and the CyP affinity fusion protein to form a complex;

d) contacting the incubate of step (c) with an affinity medium under conditions that enable the Gag-CyP affinity fusion protein complex to bind to said affinity medium;

e) determining the amount of said Gag-cyclophilin affinity fusion protein complex formation by comparison to a control sample lacking said compound;

wherein reduced binding of HIV-1 Gag to the cyclophilin affinity fusion protein is indicative of the ability of said compound to inhibit said complex formation.

2. The method of claim 1, wherein the CyP employed in the CyP affinity fusion protein is selected from the group consisting of CyP A, B, C, D, and combinations thereof.

3. The method of claim 1, wherein the CyP affinity fusion protein is a glutathione S-transferase-CyP (GST-CyP) fusion protein.

4. The method of claim 1, wherein the HIV-1 Gag protein is $Pr55^{gag}$.

5. The method of claim 1, wherein the HIV-1 Gag protein is p24.

6. The method of claim 1, wherein the affinity medium comprises glutathione-agarose beads.

7. The method of claim 1, wherein the amount of said HIV-1 Gag-CyP affinity fusion protein complex formed is determined using monoclonal antibodies.

8. The method of claim 1, wherein the amount of said HIV-1 Gag-CyP affinity fusion protein complex formed is determined using polyclonal antibodies.

9. The method of claim 1, wherein the HIV-1 Gag protein is labeled with a detectable moiety selected from the group consisting of a fluorescent label, a radioactive label, and a chemiluminescent label.

10. The method of claim 1, wherein the HIV-1 Gag-CyP affinity fusion protein complex is purified and removed from the affinity medium and the amount of Gag protein ascertained.

11. A method for identifying compounds capable of interfering with the formation of a complex between a cyclophilin (CyP) and an HIV-1 Gag affinity fusion protein, which comprises the following steps:

a) producing an HIV-1 Gag affinity fusion protein;

b) pre-incubating a compound with the HIV-1 Gag affinity fusion protein of step (a);

c) adding a CyP to the incubate of step (b) under conditions which permit the CyP and the HIV-1 Gag affinity fusion protein to form a complex;

d) contacting the incubate of step (c) with an affinity medium under conditions that enable the CyP-Gag affinity fusion protein complex to bind to said affinity medium;

e) determining the amount of said CyP-Gag affinity fusion protein complex formation by comparison to a control sample lacking said compound;

wherein reduced binding is indicative of the ability of said compound to inhibit CyP-HIV-1 Gag affinity fusion protein complex formation.

12. The method of claim 11, wherein the cyclophilin employed is selected from the group consisting of cyclophilin A, B, C, D, and combinations thereof.

13. The method of claim 11, wherein the HIV-1 Gag protein employed in the HIV-1 Gag affinity fusion protein is $Pr55^{gag}$.

14. The method of claim 11, wherein the HIV-1 Gag protein employed in the HIV-1 Gag affinity fusion protein is p24.

15. The method of claim 11, wherein the affinity medium comprises glutathione-agarose beads.

16. The method of claim 11, wherein the amount of said CyP-Gag affinity fusion protein complex formed is determined using monoclonal antibodies.

17. The method of claim 11, wherein the amount of said CyP-Gag affinity fusion protein complex formed is determined using polyclonal antibodies.

18. The method of claim 11, wherein the CyP is labeled with a detectable moiety selected from the group consisting of a fluorescent label, a radioactive label, and a chemiluminescent label.

19. The method of claim 11, wherein the CyP-HIV-1 Gag affinity fusion protein complex is purified and removed from the affinity medium and the amount of CyP protein ascertained.

20. The method of claim 1, wherein the CyP employed in the CyP affinity fusion protein is CyP A.

21. The method of claim 11, wherein the CyP employed is CyP A.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
CCCCCAAAAA AAGAGATCCC GGATCGGATC CGCGGCCGCT CTAGAACTAG TGGATCCCCC     60

GGGCTGCAGG AATTC                                                     75
```

( 2 ) INFORMATION FOR SEQ ID NO:2:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: amino acid ( x i ) SEQUENCE DESCRIPTION: SEQ ID NO:2:

```
Pro Pro Lys Lys Glu Ile Pro Asp Arg Ile Arg Gly Arg Ser Arg Thr
 1           5                   10                  15
Ser Gly Ser Pro Gly Leu Gln Glu Phe
            20              25
```

( 2 ) INFORMATION FOR SEQ ID NO:3:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
GAATTCCTAT TAGCCATGGT CAACCCCACC GTG                                  33
```

( 2 ) INFORMATION FOR SEQ ID NO:4:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: amino acid ( x i ) SEQUENCE DESCRIPTION: SEQ ID NO:4:

```
Glu Phe Leu Leu Ala Met Val Asn Pro Thr Val
 1           5                   10
```

( 2 ) INFORMATION FOR SEQ ID NO:5:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GAATTCCGGA ATTCCATCGC GGGGTCCGTC TTC    33

( 2 ) INFORMATION FOR SEQ ID NO:6:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: amino acid ( x i ) SEQUENCE DESCRIPTION: SEQ ID NO:6:

Glu Phe Arg Asn Ser Ile Ala Gly Ser Val Phe
1                   5                       10

( 2 ) INFORMATION FOR SEQ ID NO:7:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( v ) FRAGMENT TYPE: N-terminal ( x i ) SEQUENCE DESCRIPTION: SEQ ID NO:7:

CGCGCATATG CCTATAGTGC AGAACATCCA GGG    33

( 2 ) INFORMATION FOR SEQ ID NO:8:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( v ) FRAGMENT TYPE: N-terminal ( x i ) SEQUENCE DESCRIPTION: SEQ ID NO:8:

GCGCGTCGAC TTAAACTCTT GCCTTATGGC C    31

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear (i i) MOLECULE TYPE: DNA (genomic)

(i i i) HYPOTHETICAL: N (i v) ANTI-SENSE: N (v) FRAGMENT TYPE: N-terminal (x i) SEQUENCE DESCRIPTION: SEQ ID NO:9:

GATCCGCGGC CGCCATATGG 20

(2) INFORMATION FOR SEQ ID NO:10:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: DNA (genomic)

(i i i) HYPOTHETICAL: N (i v) ANTI-SENSE: N (v) FRAGMENT TYPE: N-terminal (x i) SEQUENCE DESCRIPTION: SEQ ID NO:10:

TCGACCATAT GGCGGCCGCG 20

(2) INFORMATION FOR SEQ ID NO:11:

(i) SEQUENCE CHARACTERISTICS:
(A) LENGTH: 16 base pairs
(B) TYPE: nucleic acid
(C) STRANDEDNESS: single
(D) TOPOLOGY: linear (i i) MOLECULE TYPE: DNA (genomic)

(i i i) HYPOTHETICAL: N (i v) ANTI-SENSE: N (v) FRAGMENT TYPE: N-terminal (x i) SEQUENCE DESCRIPTION: SEQ ID NO:11:

CGATGATGAA GATACC 16

(2) INFORMATION FOR SEQ ID NO:12:

(i) SEQUENCE CHARACTERISTICS:
(A) LENGTH: 16 base pairs
(B) TYPE: nucleic acid
(C) STRANDEDNESS: single
(D) TOPOLOGY: linear (i i) MOLECULE TYPE: DNA (genomic)

(i i i) HYPOTHETICAL: N (i v) ANTI-SENSE: N (v) FRAGMENT TYPE: N-terminal (x i) SEQUENCE DESCRIPTION: SEQ ID NO:12:

GGTGCACGAT GCACAG 16